United States Patent
Tanaka

(10) Patent No.: US 6,540,515 B1
(45) Date of Patent: Apr. 1, 2003

(54) CAP-TYPE MAGNETIC ATTACHMENT, DENTAL KEEPER, DENTAL MAGNET AND METHOD OF TAKING IMPRESSION USING THEREOF

(76) Inventor: Jyoji Tanaka, No. 3-15-1, Chiyoda, Kashiwa-Shi, Chiba-Ken (JP)

( * ) Notice: Subject to any disclaimer, the term of this patent is extended or adjusted under 35 U.S.C. 154(b) by 0 days.

(21) Appl. No.: 09/359,615

(22) Filed: Jul. 22, 1999

Related U.S. Application Data

(62) Division of application No. 08/805,429, filed on Feb. 25, 1997, now Pat. No. 5,954,506.

(30) Foreign Application Priority Data

Feb. 26, 1996 (JP) ................................ 8-38390

(51) Int. Cl.⁷ ................................................ A61C 8/00
(52) U.S. Cl. ..................................................... 433/189
(58) Field of Search ................................ 433/189, 213, 433/214

(56) References Cited

U.S. PATENT DOCUMENTS

| | | | |
|---|---|---|---|
| 4,302,189 A | | 11/1981 | Gillings |
| 4,530,663 A | * | 7/1985 | Portnoy ...................... 433/189 |
| 4,824,371 A | * | 4/1989 | Deutsch et al. ............. 433/189 |
| 4,911,640 A | * | 3/1990 | Schwab ....................... 433/189 |
| 4,993,950 A | * | 2/1991 | Mensor, Jr. ............. 433/189 X |
| 4,997,372 A | | 3/1991 | Shiner et al. |
| 5,421,722 A | | 6/1995 | Stemmann |
| 5,425,763 A | * | 6/1995 | Stemmann ............... 433/189 X |
| 5,636,990 A | * | 6/1997 | Stemmann ................... 433/189 |

OTHER PUBLICATIONS

The application of rare earth magnetic retention to osseointegrated implants, T. R. Jackson, *Int. J. of Oral & Maxillofacial Implants,* vol. 1, pp. 81–92, 1986.

Implants and overdentures: The osseointegrated approach with conventional and compromised applications, S. M. Parel, *Int. J. of Oral and Maxillofacial Implants,* vol. 1, pp. 93–99, 1986.

Application of magnetic attachments for implants–ITI Bonefit implants, J. Tanaka et al., *Nihon Koko Implant Gakkaishi,* vol. 8, pp. 162–168, 1995.

Y. Tanaka, *Jisei attachment,* pp. 29–33, 122–123, and 138–139, Ishiyaku Publishers, Inc., 1995.

Y. Tanaka, *Jisei attachment,* pp. 179–181, and 186–188, Ishiyaku Publishers, Inc., 1995.

Thomas G. Wilson, Jr., *ITI Implant Rinsho Manual,* pp. 74–77, Quintessence Publishing Co., Inc., 1994.

* cited by examiner

*Primary Examiner*—Nicholas D. Lucchesi
(74) *Attorney, Agent, or Firm*—Andrus, Sceales, Starke & Sawall, LLP

(57) ABSTRACT

A magnetic attachment used for retaining a dental prosthesis, comprising a male part which may be fixed to an abutment and a female part which may be fixed to said dental prosthesis. The male part of the magnetic attachment includes a head portion, which may be attached to the female part, and a fixing member used for fixing the male part to said abutment. The female part includes a cap portion having a cover portion for covering the male part.

24 Claims, 16 Drawing Sheets

(a)

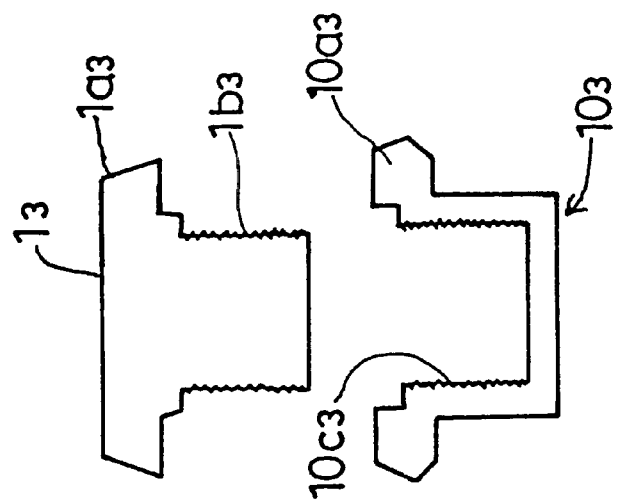
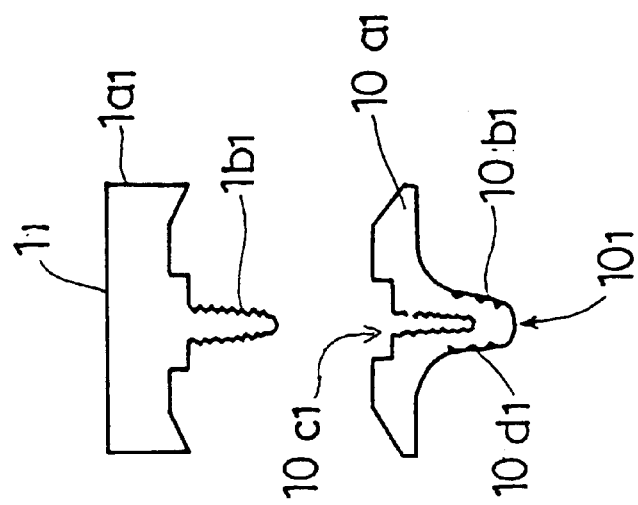
FIG. 8A  FIG. 8B  FIG. 8C

FIG. 11
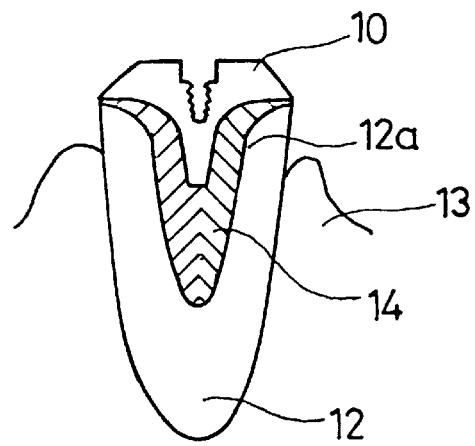
FIG. 12A
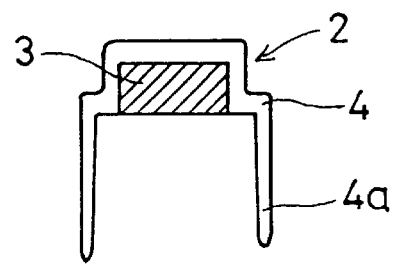
FIG. 12B
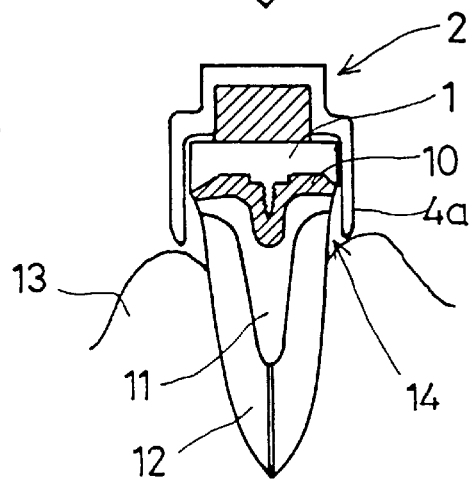

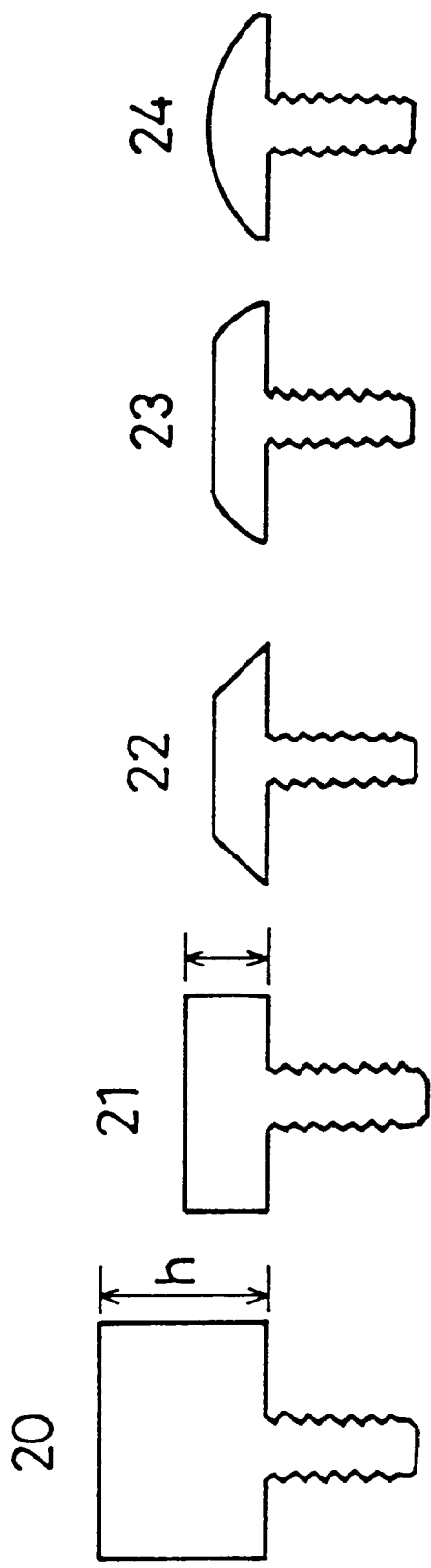

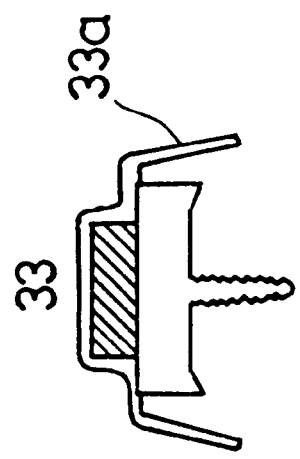
FIG. 15A  FIG. 15B  FIG. 15C  FIG. 15D
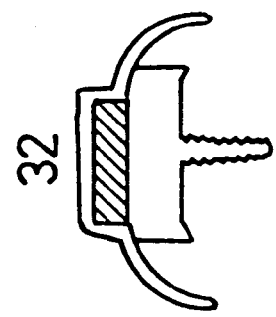
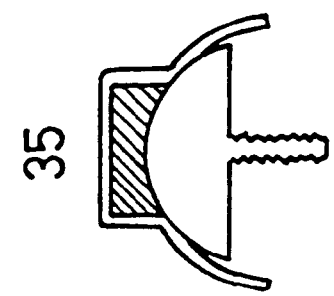
FIG. 15E  FIG. 15F
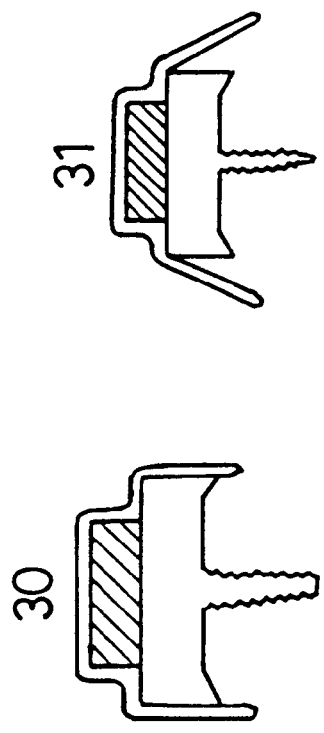
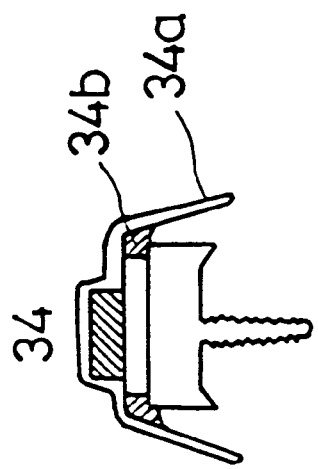

FIG. 18
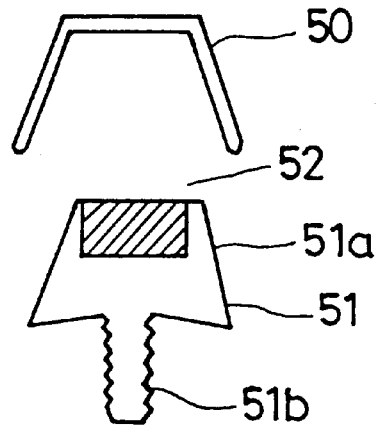
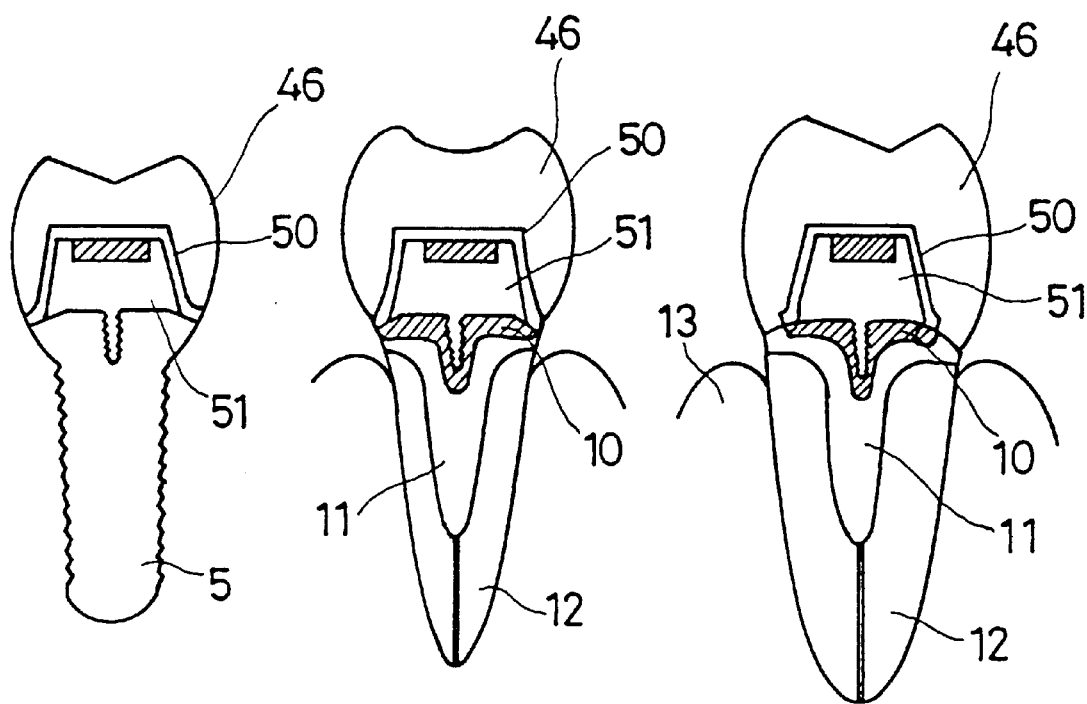
FIG. 19A  FIG. 19B  FIG. 19C

CAP-TYPE MAGNETIC ATTACHMENT, DENTAL KEEPER, DENTAL MAGNET AND METHOD OF TAKING IMPRESSION USING THEREOF

CROSS-REFERENCE TO RELATED APPLICATIONS

The present application is a divisional application of copending U.S. patent application, appln. Ser. No. 08/805,429, filed Feb. 25, 1997, and now U.S. Pat. No. 5,954,506.

BACKGROUND OF THE INVENTION

1. Field of the Invention

The present invention generally relates to a dental attachment, a dental keeper, a dental magnet and a method for taking an impression using thereof, and more particularly, to a dental attachment used for dental prostheses such as a denture, a crown and a crown-and-bridge set, and a dental keeper of the dental attachment which use magnetic force for retention and a method for taking an impression using thereof.

2. Description of the Related Art

Various methods have been used for retaining a dental prosthesis such as a denture, a crown and a crown-and-bridge set in medicine and dentistry. For instance, methods which use a mechanical attachment used to be among the main methods for the purpose. These days, however, a magnetic attachment (also called as a magnetic retention, a magnetic system, a magnetic anchor attachment, rare earth attachment and so on) utilizing a potent magnet of small size has been developed and applied clinically.

In general, a magnetic attachment is comprised of a magnetic assembly, which is provided with a dental prosthesis, and a dental keeper made of a steel plate (usually a stainless steel plate), which may be attached to an abutment. Thus, the dental keeper is attracted to the magnetic assembly by the magnetic force and the denture prosthesis is attached to the abutment.

FIG. 1 is a diagram for explaining an example of a conventional dental prosthesis (denture) using a magnetic attachment. The dental prosthesis 155 includes a denture portion comprising a magnet 152, a resin base 156 and an artificial tooth 157, and a dental keeper 151 formed integrally with a root cap 153. The numeral 158 indicates gingival tissues and the numeral 159 indicates a root of a tooth. The dental keeper 151, which is made of a magnetic stainless steel (or magnetic metal), is embedded in the upper portion of the root cap 153 so that the denture portion is fixed to the root cap 153 through the magnetic force of the magnet 152.

The above-mentioned magnetic attachment has advantages in that an excessive stress on the abutments at the time of insertion and removal of a dental prosthesis may be eliminated, unlike the mechanical attachments, and the insertion/removal operation of the dental prosthesis itself is very easy. Also, the degree of the holding force of the magnet used may be measured and it is not attenuated during a long-term use. Moreover, the magnetic attachments are non-directional for the insertion and removal of dental prostheses and they transmit little lateral force to the abutments.

However, when the magnetic assembly and the dental keeper are positioned at their respective locations manually, it is difficult to exactly position them at a desired location, and it requires a skillful hand for carrying out the operation.

Also, since the dental keeper is embedded in the upper portion of the root cap, it is difficult to adjust the position of the dental keeper when a shift in location of the dental keeper has occurred. Moreover, there have been reports of accidents in which dental prostheses were faultily detached due to an instable attachment of the dental keeper and the magnetic assembly.

On the other hand, it has been proposed to make the dental keeper of a magnetic attachment removable since there is a danger that the magnetic attachment has an effect on biological measurements which utilize a magnetic force such as MRI. However, the proposed method is a method in which the dental keeper is embedded completely in the root cap. Therefore, according to the above method, the size of the dental keeper must be reduced since there is additional space needed for a metal part which is used for covering the dental keeper. Hence, it is likely that the operation according to the above method becomes tedious and complicated.

SUMMARY OF THE INVENTION

Accordingly, it is a general object of this invention to provide a magnetic attachment used for retaining a dental prosthesis in which the above mentioned problems are eliminated.

A more specific object of the present invention is to provide a magnetic attachment used for retaining a dental prosthesis by which a dental prosthesis having a magnetic assembly (i.e., female part of magnetic attachment) may be firmly attached to a dental keeper (i.e., male part of magnetic attachment) removably fixed to an abutment.

Another object of the present invention is to provide a magnetic assembly (i.e., female part of magnetic attachment) and a dental keeper (i.e., male part of magnetic attachment) which are appropriate for use in the above magnetic attachment.

Yet another object of the present invention is to provide an intermediate metal which may be used for fixing the dental keeper to a natural tooth.

Yet another object of the present invention is to provide a magnetic attachment which may be used for a method for taking an impression in dentistry.

The objects described above are achieved by a magnetic attachment used for retaining a dental prosthesis, comprising a male part which may be fixed to an abutment and a female part which may be fixed to the dental prosthesis, wherein the male part includes a head portion which may be attached to the female part and a fixing member used for fixing the male part to the abutment, and the female part includes a cap portion having a cover portion for covering the male part.

According to the above magnetic attachment, since the male part may be firmly covered by the cover portion of the cap portion, the attachment of the male part and the female part of the magnetic attachment can be accurately made.

The objects described above are also achieved by the magnetic attachment, wherein the fixing member is detachable from the male part.

According to the above magnetic attachment, since the fixing member is detachable from the male part, a male part having an irregular shape and not easily rotated may be used in accordance with the condition of an abutment.

The objects described above are also achieved by the magnetic attachment, wherein a magnet is included in one of the male part, the female part, and the male part and the female part.

According to the above magnetic attachment, since the magnet may be located in the male part, the female part or both, the range of the application of the magnetic attachment may be widened and, for instance, a female part including a larger magnet in size having an increased magnetic force may be used for a case in which there is not much clearance present. Also, since it becomes possible to directly cast a crown and a bridge to a female part, the precision of attachment may be improved.

The objects described above are also achieved by the magnetic attachment, wherein the male part is removable from the abutment.

According to the above magnetic attachment, since the male part is removable from the abutment, a danger that the magnetic attachment may effect the result of a biological measurement which utilizes a magnetic force such as MRI can be avoided.

The objects described above are achieved by a male part of a magnetic attachment used in dentistry, wherein the male part includes a head portion and a fixing member which is used for fixing the male part to an abutment, the head portion, when fixed, being projected from the upper surface of the abutment, and the male part may be used singly without being in combination with a female part of magnetic attachment.

According to the above male part of magnetic attachment, since the head portion of the male part is projected from the upper surface of the abutment when it is fixed, it is easy to cover the head portion with the female part, and hence an attachment of the male part and the female part may be carried out accurately.

The objects described above are also achieved by the male part of magnetic attachment, wherein the male part comprises one of a magnet, a magnetic metal, and a magnet and a magnetic metal.

According to the above male part of magnetic attachment, since the male part may include, unlike a conventional male part, either a magnet or a magnetic metal, the range of the application of the male part may be widened, and, for instance, it becomes possible to directly attach a crown or a crown-and-bridge set to the male part using a magnetic force.

The objects described above are also achieved by the male part of magnetic attachment, wherein the fixing member is detachable from the male part.

According to the above male part of magnetic attachment, since the fixing member is detachable from the male part, a male part having an irregular shape and not easily rotated may be used in accordance with the condition of an abutment. Also, the male part and the fixing member may be easily produced using different materials, and therefore, the strength and the properties such as an anti-corrosive property of the male part may be improved.

The objects described above are also achieved by the male part of magnetic attachment, wherein the male part is removable from the abutment.

According to the above male part of magnetic attachment, since the male part is removable from the abutment, a danger that the magnetic attachment may effect the result of a biological measurement which utilizes a magnetic force such as MRI can be avoided.

The objects described above are achieved by a female part of a magnetic attachment used in dentistry, wherein the female part includes a cap portion having a cover portion for covering a male part of the magnetic attachment.

According to the above female part of the magnetic attachment, since the female part has the cap portion having a cover portion for covering a male part, an attachment of the male part and the female part may be carried out accurately. Also, the cover portion may prevent a flow of resin into an unwanted portion when the resin is used to adhere the female part to a dental prosthesis.

The objects described above are also achieved by the female part of the magnetic attachment, wherein the female part comprises one of a magnet, a magnetic metal, and a magnet and a magnetic metal.

According to the above female part of the magnetic attachment, since the female part may include, unlike a conventional female part, either a magnet or a magnetic metal, the range of the application of the female part may be widened, and, for instance, a female part including a larger magnet in size having an increased magnetic force may be used for a case in which there is not much clearance present. Also, since it becomes possible to directly cast a crown and a bridge to a female part, the precision of attachment may be improved.

The objects described above are also achieved by the female part of the magnetic attachment, wherein the cap portion is formed of one of a resin, a metal and an elastic member.

According to the above female part of the magnetic attachment, since the cap portion is formed of a resin, a metal or an elastic member, it is possible, for example, to obtain a depressurizing effect using an elastic member.

The objects described above are achieved by an intermediate metal part for fixing a male part of a magnetic attachment used in dentistry, wherein the intermediate metal part has a fixing portion for removably fixing the male part of the magnetic attachment.

According to the above intermediate metal part, it becomes possible to fix the male part of the magnetic attachment to a natural tooth via the intermediate metal part. Also, since the shape of the intermediate metal part may be easily changed in accordance with the condition of a root of a tooth, a desired male part of a magnetic attachment may be employed due to the presence of the intermediate metal part. Moreover, since the fixing portion for removably fixing the male part of the magnetic attachment is provided with the intermediate metal part, a danger that the magnetic attachment may effect the result of a biological measurement which utilizes a magnetic force such as MRI can be avoided.

The objects described above are also achieved by the intermediate metal part for fixing a male part of a magnetic attachment used in dentistry, wherein a female part of the magnetic attachment is used together with the male part of the magnetic attachment.

According to the above intermediate metal part, it becomes possible to use the female part of the magnetic attachment in combination with the male part of the magnetic attachment for a natural tooth.

The objects described above are also achieved by the intermediate metal part for fixing a male part of a magnetic attachment used in dentistry, wherein the male part of the magnetic attachment includes a head portion and a fixing member which is used for fixing the male part part to the intermediate metal, the head portion, when fixed, being projected from the upper surface of the abutment, and the male part may be used singly without being in combination with a female part of the magnetic attachment.

According to the above intermediate metal part, it becomes possible to fix the male part of the magnetic attachment to a natural tooth via the intermediate metal part.

Also, since the shape of the intermediate metal part may be easily changed in accordance with the condition of a root of a tooth, a desired male part of the magnetic attachment may be employed due to the presence of the intermediate metal part.

The objects described above are achieved by a magnetic attachment used for taking an impression in dentistry, comprising a male part which may be fixed to an abutment and a female part which may be attached to the male part, wherein the male part includes a head portion which may be attached to the female part and a fixing member used for fixing the male part to the abutment, and the female part includes a cap portion having a cover portion for covering the male part.

According to the above magnetic attachment used for taking an impression, it is possible to take an impression of an abutment without using any complicated devices or materials which are required for conventional methods for taking an impression, and hence the process may be simplified and carried out easily.

The objects described above are also achieved by the magnetic attachment used for taking an impression, wherein the fixing member is detachable from the male part.

According to the above magnetic attachment used for taking an impression, since the fixing member is detachable from the male part, a male part having an irregular shape and not easily rotated may be used in accordance with the condition of an abutment.

The objects described above are also achieved by the magnetic attachment used for taking an impression, wherein a magnet is included in one of the male part, the female part, and the male part and the female part.

According to the above magnetic attachment used for taking an impression, since the magnet may be located in the male part, the female part or both, the range of the application of the magnetic attachment may be widened.

The objects described above are achieved by a method for taking an impression in dentistry comprising the steps in which a magnetic attachment including a male part which may be fixed to an abutment and a female part which may be attached to the male part is used, wherein the male part includes a head portion which may be attached to the female part and a fixing member used for fixing the male part to the abutment, and the female part includes a cap portion having a cover portion for covering the male part.

The objects described above are also achieved by the method for taking an impression, comprising the steps of: (a) fixing the male part to the abutment in an oral cavity, (b) attaching the female part to the male part, (c) pressing an impression material to the female part, (d) taking out the impression material in which the female part is embedded from the oral cavity after the impression material is cured, (e) attaching an analog of the abutment to the female part embedded in the impression material via the male part which is fixed to the analog, (f) applying plaster material onto the analog and the impression material, (g) taking out the plaster material together with the analog, to which the male part is fixed, from the impression material after the plaster material is cured, and (h) removing the second male part from the analog to form a replica of the abutment in the oral cavity.

According to the above method for taking an impression, it is possible to take an impression of an abutment without using any complicated devices or materials which are required for conventional methods for taking an impression, and hence the process may be simplified and carried out easily.

Other objects and further features of the present invention will be apparent from the following detailed description when read in conjunction with the accompanied drawings.

BRIEF DESCRIPTION OF THE DRAWINGS

FIG. 8A is a diagram showing an intermediate metal which may be used for making a keeper removable when a magnetic attachment according to the present invention is applied to natural teeth;

FIG. 8B is a diagram showing another embodiment of the intermediate metal shown in FIG. 8A;

FIG. 8C is a diagram also showing another embodiment of the intermediate metal shown in FIG. 8A;

FIG. 11 is a diagram showing a case in which an intermediate metal is attached to a tooth root using another method;

FIG. 12A is a diagram for explaining a case in which the cap-type magnetic assembly shown in FIG. 2A is attached to the keeper which is adhered to the tooth root through the intermediate metal;

FIG. 12B is a diagram for explaining a case in which the cap-type magnetic assembly shown in FIG. 2A is attached to the keeper which is adhered to the tooth root through the intermediate metal;

FIG. 14A is a diagram for showing a variation of the male part of the magnetic attachment according to the present invention;

FIG. 14B is a diagram for showing a variation of the male part of the magnetic attachment according to the present invention;

FIG. 14C is a diagram for showing a variation of the male part of the magnetic attachment according to the present invention;

FIG. 14D is a diagram for showing a variation of the male part of the magnetic attachment according to the present invention;

FIG. 14E is a diagram for showing a variation of the male part of the magnetic attachment according to the present invention;

FIG. 14F is a diagram for showing a magnet which may be used in combination with the male part of the magnetic attachment shown in FIG. 14E;

FIG. 15A is a diagram for showing a variation of the female part of the magnetic attachment according to the present invention;

FIG. 15B is a diagram for showing a variation of the female part of the magnetic attachment according to the present invention;

FIG. 15C is a diagram for showing a variation of the female part of the magnetic attachment according to the present invention;

FIG. 15D is a diagram for showing a variation of the female part of the magnetic attachment according to the present invention;

FIG. 15E is a diagram for showing a variation of the female part of the magnetic attachment according to the present invention;

FIG. 15F is a diagram for showing a variation of the female part of the magnetic attachment according to the present invention;

FIG. 18 is a diagram showing another modified embodiment of the magnetic attachment according to the present invention;

FIG. 19A is a diagram for showing an embodiment in which the magnetic attachment shown in FIG. 18 is applied to fix a crown;

FIG. 19B is a diagram for showing an embodiment in which the magnetic attachment shown in FIG. 18 is applied to fix a crown;

FIG. 19C is a diagram for showing an embodiment in which the magnetic attachment shown in FIG. 18 is applied to fix a crown;

DETAILED DESCRIPTION OF THE PREFERRED EMBODIMENTS

In the following, a principle and embodiments of the present invention will be described with reference to the accompanying drawings.

Figure 2A:
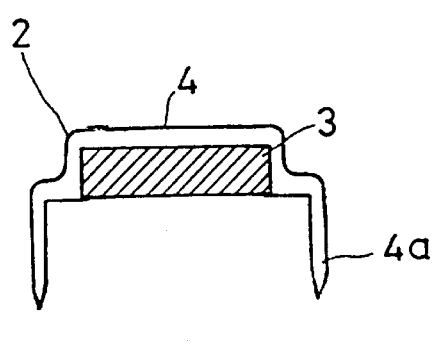
FIG. 2A is a diagram showing a cross-sectional view of a cap-type magnetic assembly according to the present invention.
Figure 2B:
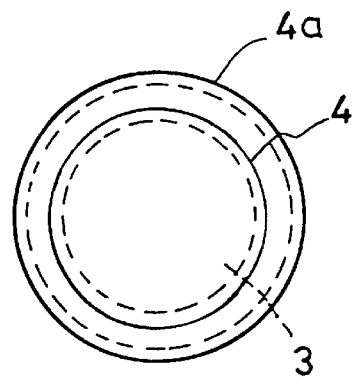
FIG. 2B is diagram showing a top view of the cap-type magnetic assembly shown in FIG. 2A.
Figure 3A:
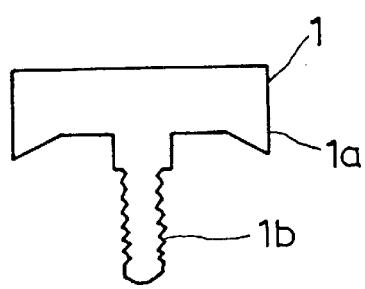
FIG. 3A is a diagram showing a cross-sectional view of a dental keeper according to the present invention.
Figure 3B:
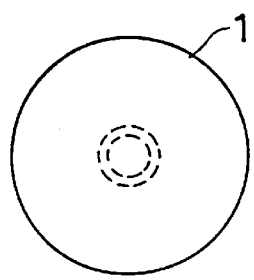
FIG. 3B is a diagram showing a top view of the keeper shown in FIG. 3A.
Figure 4:
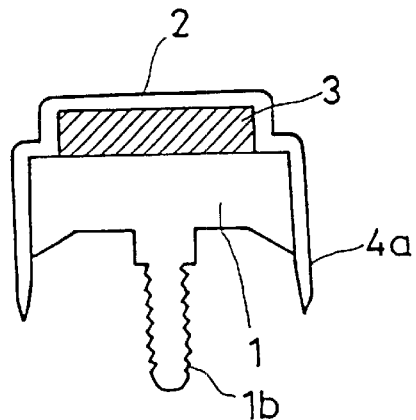
FIG. 4 is a diagram showing the keeper and the cap-type magnetic assembly in an attached state.

FIGS. 2A through 4 are diagrams for explaining the basic structure of the magnetic attachment according to the present invention. FIG. 2A shows a cross-sectional view of a cap-type magnetic assembly 2 which includes a magnet 3, a cap portion 4 and a cover portion 4a, and FIG. 2B is a top view of the cap-type magnetic assembly 2 shown in FIG. 2A. FIG. 3A shows a cross-sectional view of a dental keeper 1 (hereinafter also referred to as a keeper) which includes a head portion 1a and a screw portion 1b, and FIG. 3B is a top view of the keeper 1 shown in FIG. 3A. FIG. 4 is a diagram showing the keeper 1 and the cap-type magnetic assembly 2 in an attached state.

The magnetic attachment according to the present invention is generally comprised of the cap-type magnetic assembly 2 shown in FIGS. 2A and 2B and the dental keeper 1 shown in FIGS. 3A and 3B. The keeper 1 may be attached to a root cap which is fixed to an abutment tooth or to an osteo-integrated implant to form a male part of the magnetic attachment whereas the cap-type magnetic assembly 2, which may be attached to a dental prosthesis member such as an artificial tooth or a crown, forms a female part of the magnetic attachment.

The dental keeper 1 may be made of a known magnetic metal such as a magnetic stainless steel and, as mentioned above, is comprised of the head portion 1a, which attracts the magnet 3 of the cap-type magnetic assembly 2 and the screw portion 1b (i.e., a fixing member) used for fixing the keeper 1 to, for example, a root cap of an abutment.

However, according to the present invention, the dental keeper 1 may be made of a magnet covered by, for instance, a resin or an elastic member depending on its purpose. Also, many variations in shape and material of the dental keeper 1 may be made and, for instance, a hole may be provided in the center of the keeper instead of the screw portion 1b so that the dental keeper may be fixed by a screw member (i.e., a fixing member) having various characteristics. This will be described in detail later.

The cap-type magnetic assembly 2 is generally comprised of the magnet 3, and the cap portion 4 having the cover portion 4a. The magnet 3 may be integrally formed with the cap portion 4 by using, for instance, an appropriate resin or an elastic member as a cap portion material and putting the magnet 3 into the resin or elastic member during a molding process.

The magnet 3 used in the present invention may be made of any known magnet material and, in general, has a cylindrical shape. However, its shape is not particularly limited and any shape of magnet may be used depending on the situation.

The cap portion 4, in general, has a circular shape when looking down from the top so that its shape may suitably be fit to the shape of the magnet 3. On the other hand, the cover portion 4a extends downwards from the periphery of the cap portion 4. In general, the inner diameter of the cover portion 4a is adjusted so that it becomes equal to the outer diameter of the keeper 1.

According to the present invention, however, the magnet 3 of the cap-type magnetic assembly 2 may be substituted by a magnetic metal if the dental keeper 1 includes a magnet, and in that case the cap-type magnetic assembly 2 may be called a cap-type magnetic metal assembly 2. That is, there are three possible combinations of the keeper (i.e., the male part of the attachment) and the cap-type magnet assembly or the cap-type magnetic metal assembly (i.e., the female part of the attachment) and they are: magnetic metal-magnet; magnet-magnetic metal; and magnet-magnet. This will also be described in detail later.

As shown in FIG. 4, when the cap-type magnetic assembly 2 is attached to the keeper 1, the keeper 1, which forms the male part of the attachment as mentioned above, is located inside of the cover portion 4a of the cap-type magnetic assembly 2, which forms the female part of the attachment. The keeper 1 is attracted to the cap-type magnetic assembly 2 by the magnetic force and they are attached together.

Figure 1:
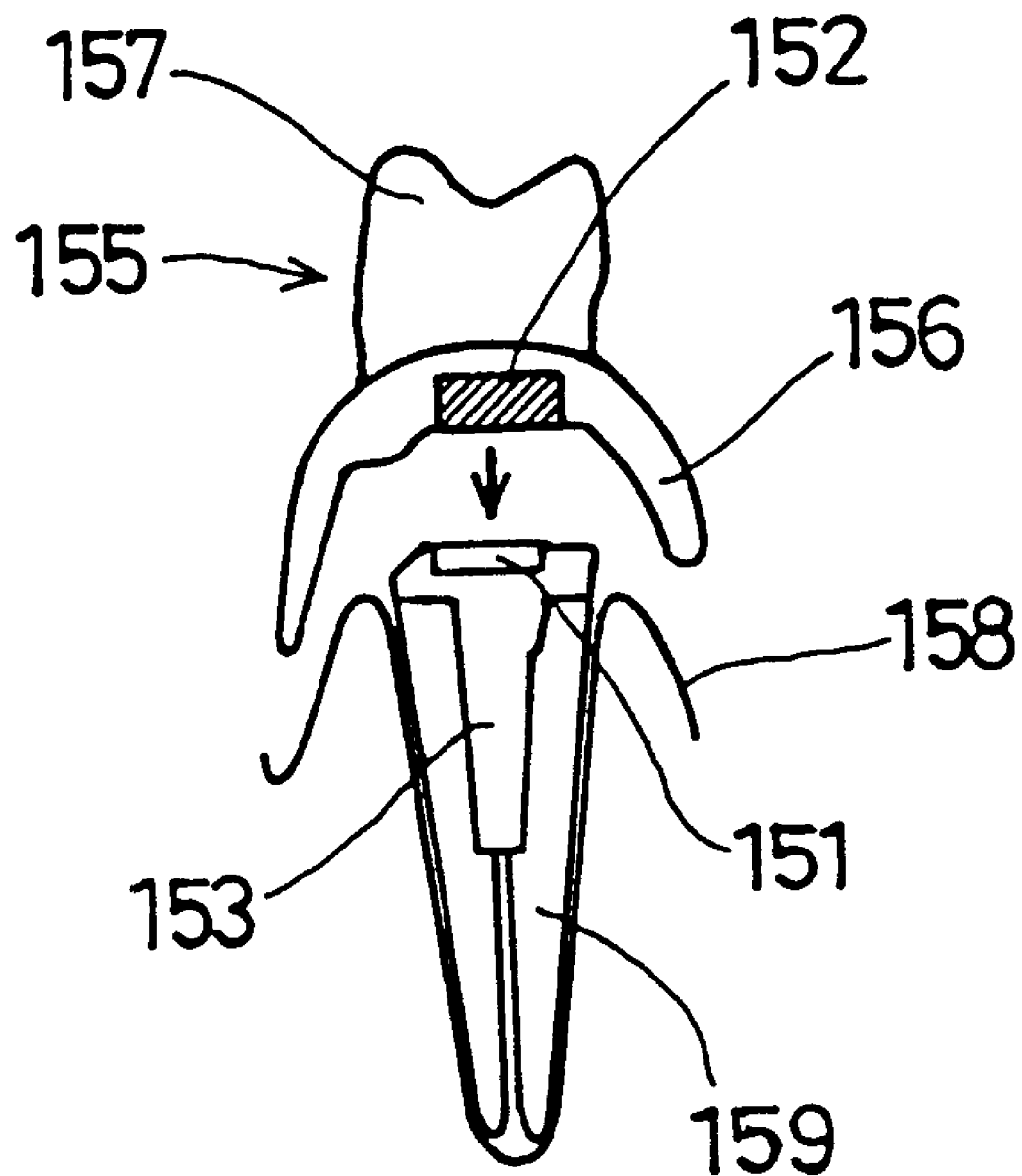
FIG. 1 is a diagram for explaining an example of a conventional denture using a magnetic attachment.

Note that FIG. 4 is an explanatory diagram showing an attached state of the keeper 1 and the cap-type magnetic assembly 2 and in practical dental treatment using a dental prosthesis, the keeper is generally fixed to the abutment by the screw portion 1b or a fixing member and the cap-type magnetic assembly 2 is adhered to a denture portion as shown in FIG. 1. Also note that the definition of the term "abutment" used in this specification includes both natural teeth and implants.

FIGS. 5A through 6B are diagrams for explaining a case in which the magnetic attachment according to the present invention is applied to a conventional implant. In FIGS. 5A through 6B, elements which are the same as the ones in FIGS. 2A through 4 are indicated by the same reference numerals and the explanation thereof will be omitted.

Figure 5A:
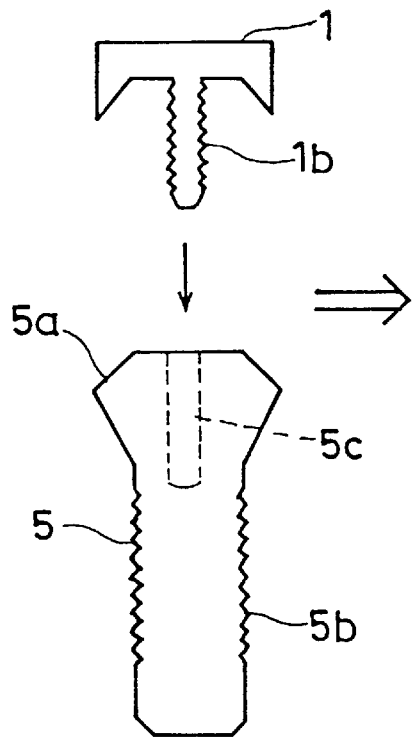
FIG. 5A is a diagram for explaining a case in which a magnetic attachment according to the present invention is applied to a conventional implant.
Figure 5B:
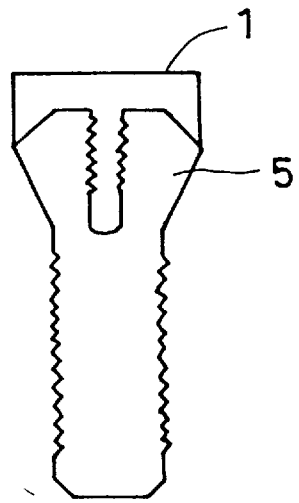
FIG. 5B is a diagram for explaining a case in which a magnetic attachment according to the present invention is applied to a conventional implant.

As shown in FIG. 5A, an implant 5 is comprised of a head portion 5a, a screw portion 5b and a screw hole 5c. The implant 5 may be made of titanium or alloys thereof and can be firmly fixed to a bone by the screw portion 5b. On the other hand, the screw portion 1b of the keeper 1 according to this embodiment is formed so as to be engaged with the screw hole 5c of the implant 5. By adjusting the shape of the keeper 1 to the outer shape of the head portion 5a of the implant 5, it is possible to apply the magnetic attachment according to the present invention to a conventional implant as shown in FIG. 5B. That is, the screw portion 1b of the keeper 1 may be driven into the screw hole 5c of the implant 5 because the shape of the keeper 1 is adjusted according to the shape of the head portion 5a of the implant 5.

Figure 6A:
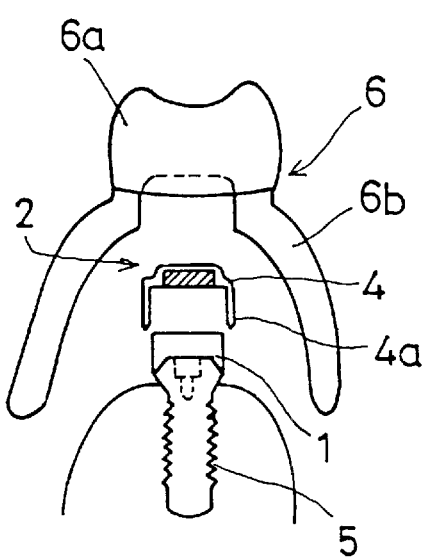
FIG. 6A is a diagram for explaining a case in which a magnetic attachment according to the present invention is applied to a conventional implant.
Figure 6B:
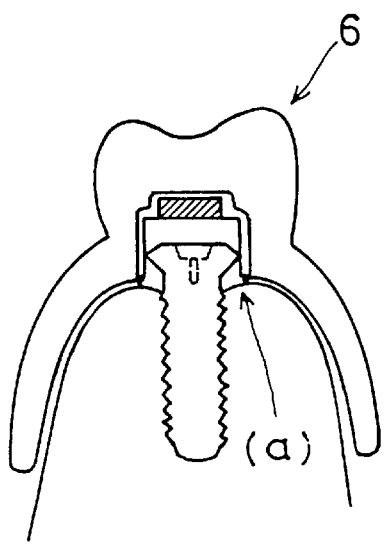
FIG. 6B is a diagram for explaining a case in which a magnetic attachment according to the present invention is applied to a conventional implant.

FIG. 6A is a diagram for explaining an attachment of a denture portion 6 to the keeper 1 which is fixed to the implant 5 as shown in FIG. 5B. The denture portion 6 is comprised of an artificial tooth 6a, a resin base 6b and the cap-type magnetic assembly 2 as explained above. FIG. 6B is a diagram showing an adhered state of the denture portion 6 with the keeper 1 of the implant 5.

In general, the cap-type magnetic assembly 2 is fixed to the resin base 6b of the denture portion 6 using a self-hardening resin. Here, an example of a method in which the cap-type magnetic assembly 2 is fixed to the denture portion 6 in the oral cavity will be explained.

First of all, the keeper 1 is fixed to the implant 5, which is fixed to a bone, by driving the screw portion 1b into the screw hole 5c formed in the head portion 5a of the implant 5. Then, the cap-type magnetic assembly 2 is attached to the keeper 1 as shown in FIG. 4. As explained above, since the cap-type magnetic assembly 2 is attached to the keeper 1 so that the cover portion 4a of the cap portion 4 covers the keeper 1 which is fixed to the head portion 5a of the implant 5, it is very easy to carry out a positioning of the cap-type magnetic assembly 2 (the denture portion 6). Also, a shift in position of the magnet 3 attracting the keeper 1 will not occur.

After that, a self-hardening resin is filled in a cap loading portion of the denture portion 6 and the denture portion 6 is mounted on the cap portion 4 of the cap-type magnetic assembly 2. Finally, the denture portion 6 is firmly pressed to the cap-type magnetic assembly 2 manually or by the force generated by the patient's jaw in order to strongly fix the cap portion 4 of the cap-type magnetic assembly 2 to the resin base 6b of the denture portion 6 upon cure of the self-hardening resin.

Since the denture portion 6, to which the cap-type magnetic assembly 2 is fixed, is retained by the magnetic holding force, it is easy to take out the denture portion 6 from the abutment whenever necessary.

Also, when it is required to remove a keeper, which includes a magnet, as in the case to perform an MRI measurement, the keeper may be taken out by unscrewing the screw portion 1b. Moreover, according to the present invention, since the keeper may be taken out, it is possible to reconstruct or repair the keeper at a later occasion.

According to the above-mentioned method in which the cap-type magnetic assembly 2 is fixed to a dental prosthesis in the oral cavity, it is possible to ideally form surrounding parts of the cap-type magnetic assembly 2 in relation to a condition and shape of the gingival around the abutment. For instance, the cover portion 4a of the cap-type magnetic assembly 2 prevents the self-hardening resin from flowing into a non-allowable portion which is indicated by the arrow "a" shown in FIG. 6B.

Next, an embodiment of the present invention in which the magnetic attachment is applied to a remaining root of a natural tooth will be explained with reference to FIGS. 7A and 7B.

Figure 7A:
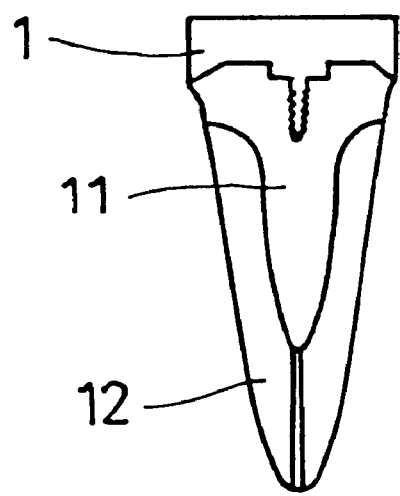
FIG. 7A is a diagram showing a case in which a keeper is directly fixed to a root cap whose width is smaller than the diameter of the keeper.

FIG. 7A is a diagram showing a case in which the keeper 1 is directly fixed to a root cap 11 whose width is smaller than the diameter of the keeper 1. FIG. 7B is a diagram showing the same case shown in FIG. 7A except that the width of the root cap 11 is larger than the diameter of the keeper 1. Note that a root of a tooth is indicated by the numeral 12 in both figures.

Figure 7B:
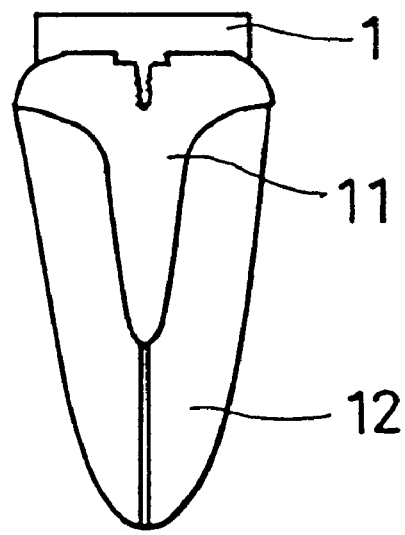
FIG. 7B is a diagram showing the same case shown in FIG. 7A except that the width of a root cap is larger than the diameter of the keeper.

As shown in FIGS. 7A and 7B, although the keeper 1 may be directly adhered to the root cap 11 which may be cemented to the root of the tooth, it is also possible to make the keeper 1 removable, for instance, by providing an intermediate metal part having a screw hole which may be engaged with the screw-type fixing member of the keeper.

FIGS. 8A through 8C, respectively, show an embodiment of a removable keeper (a male part of an attachment) in combination with a respective intermediate metal.

FIG. 8A is a diagram showing an intermediate metal part $10_1$ which may be used for making the keeper $1_1$ removable when the magnetic attachment according to the present invention is applied to natural teeth. As shown in FIG. 8A, the intermediate metal part $10_1$ is comprised of a head portion $10a_1$ and a bottom portion $10b_1$. The head portion $10a_1$ has a shape which matches the shape of the lower part of a head portion $1a_1$ of the keeper $1_1$ and a screw hole $10c_1$, in which a fixing member $1b_1$ of the keeper $1_1$ is driven, is provided with the head portion $10a_1$. Undercut portions $10d_1$ may be formed on the surface of the bottom portion $10b_1$, if necessary, to enhance the bonding strength of the intermediate metal $10_1$ to the root cap when it is embedded therein which is adhered to a natural tooth.

FIG. 8B shows another example of the intermediate metal part ($10_2$) which may be used in combination with the keeper ($1_2$) shown in the same figure. As shown in FIG. 8B, the intermediate metal part $10_2$ according to this embodiment is comprised of a plate portion $10a_2$ having a male thread portion $10c_2$ projecting from the upper surface of the plate portion $10a_2$. Undercut portions $10d_2$ may be formed on the lower surface of the plate portion $10a_2$. The keeper $1_2$, which is fixed to the intermediate metal $10_2$, is provided with a screw hole $1b_2$ engaged with the thread portion $10c_2$ and has a shape which matches the shape of the intermediate metal part $10_2$.

FIG. 8C shows another example of the intermediate metal part ($10_3$) which may be used in combination with the keeper ($1_3$) shown in the same figure. As shown in FIG. 8C, the intermediate metal part $10_3$ according to this embodiment is comprised of a screw thread portion $10c_3$ and an engaging head portion $10a_3$. The keeper $1_3$, which is fixed to the intermediate metal part $10_3$, has a male thread portion $1b_3$ to be driven in the screw thread portion $10c_3$ and a head portion $1a_3$ which may be engaged with the engaging head portion $10a_3$ of the intermediate metal part $10_3$.

As shown in FIGS. 8A through 8C, various combinations of the intermediate metal part and the keepers may be provided in accordance with the shape or condition of the root cap, or the shape of the keeper used.

Figure 9A:
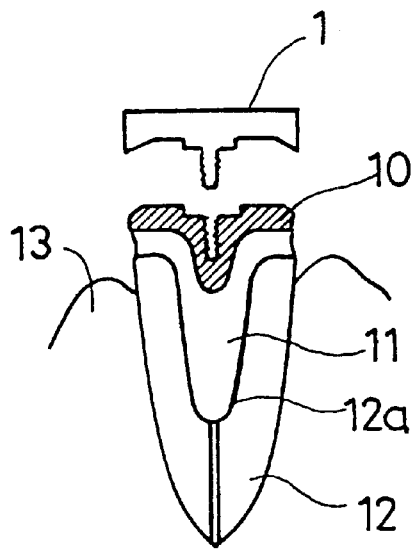
FIG. 9A is a diagram for showing a root cap, in which an intermediate metal is embedded, in the oral cavity.
Figure 9B:
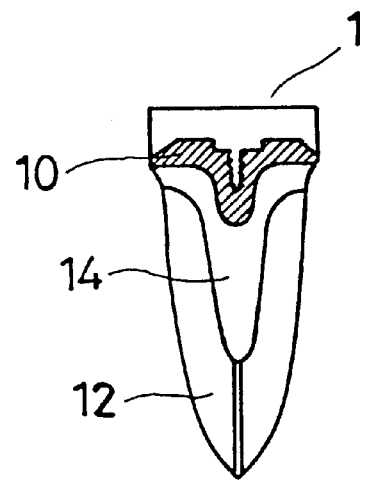
FIG. 9B is a diagram for showing a root cap, in which an intermediate metal is embedded, in the oral cavity.
Figure 10A:
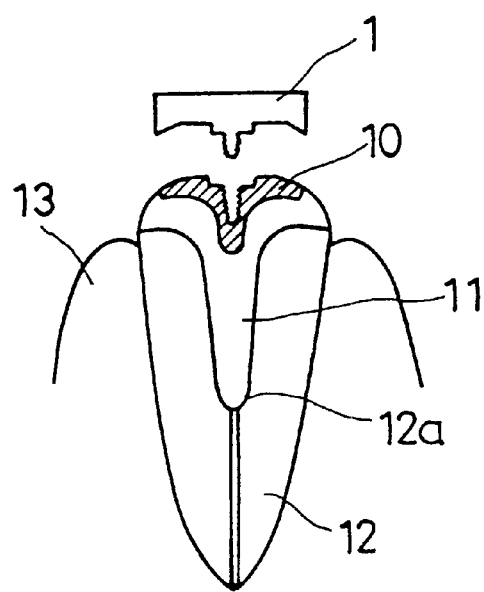
FIG. 10A is a diagram for showing a root cap, in which an intermediate metal is embedded, in the oral cavity.
Figure 10B:
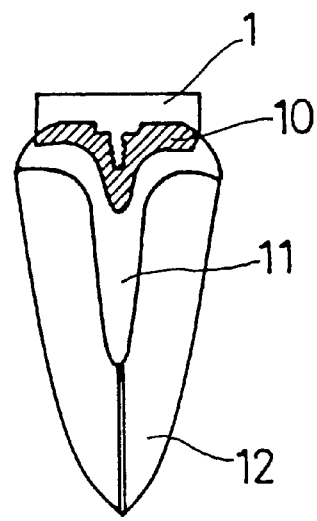
FIG. 10B is a diagram for showing a root cap, in which an intermediate metal is embedded, in the oral cavity.

FIGS. 9A through 10B are diagram for showing a root cap 11, in which the intermediate metal part 10 is embedded, in the oral cavity. FIG. 9A is a diagram showing a case in which the width of the root of tooth 12 is smaller than the diameter of the intermediate metal part 10, and FIG. 9B is a diagram showing a state in which the keeper 1 is driven into the intermediate metal part 10. FIG. 10A is a diagram showing a case in which the width of the root of tooth 12 is larger than the diameter of the intermediate metal part 10 and FIG. 10B is a diagram showing a state in which the keeper 1 is driven into the intermediate metal part 10. Thus, the keeper 1 may be attached to any type or condition of tooth root using the intermediate metal part 10 which may be prepared in accordance with the type of the keeper The root cap 11 is made of a conventional dental metal and is usually cemented to a concave portion 12a formed in the root of the tooth 12. This process may be carried out by making a mold of the concave portion 12a using, for instance, a wax, in which an intermediate metal 10 is incorporated, and applying a dental metal used for the root cap 11 to the mold so that the dental metal part is adhered to the intermediate metal part 10. The thus-formed root cap 11 integrated with the intermediate metal part 10 is cemented to the concave portion 12a of the root of the tooth 12.

As mentioned above, dental prostheses such as a denture and a crown having a cap-type magnetic assembly (i.e. female part) according to the present invention may be attached to the keeper (i.e., male part) thus fixed to the intermediate metal part.

According to the present invention, it is possible to use a desired keeper for various conditions of a tooth root by preparing various kinds of intermediate metal part for the keeper.

FIG. 11 is a diagram showing a case in which an intermediate metal part 10 is attached to a tooth root using another method. In this case, the intermediate metal part 10 is fixed to a concave portion 12a of a root of a tooth 12 using a material such as a resin 14.

FIGS. 12A and 12B are diagrams for explaining a case in which the cap-type magnetic assembly 2 shown in FIG. 2A is attached to the keeper 1 which is adhered to the tooth root 12 through the intermediate metal part as shown in FIG. 9B. The keeper 1 fixed to the intermediate metal part 10 is attached to the cap-type magnetic assembly 2 by a magnetic force.

As shown in FIG. 12B, the keeper 1 according to the present invention is (removably) fixed to the root cap 11 in a state in which the keeper 1 is projected from the root cap 11 and the cover portion 4a of the cap-type magnetic assembly 2 covers the thus-projected keeper 1. Therefore, an accurate positioning of the cap-type magnetic assembly 2 with respect to the keeper 1 may be readily performed and the once determined position is easily maintained.

When the magnetic attachment according to this embodiment is applied to a denture, the above method described for FIGS. 6A and 6B may be used to obtain a denture in which the cap portion 4 is adhered to a resin base of the denture. When the denture portion is adhered to the cap-type magnetic assembly 2, a self-hardening resin is generally used as mentioned above and is applied between the two. According to the present invention, since the cover portion 4a of the cap portion 4 covers the tooth root 12, the root cap 11 and the intermediate metal part 10, a flow of the resin into forbidden portions such as a space indicated by the arrow 14 shown in FIG. 12B can be prevented. If this space is filled with the resin, the cap-type magnetic assembly 2 is permanently fixed to the root cap 11 and the magnetic attachment is no longer removable.

Figure 13A:
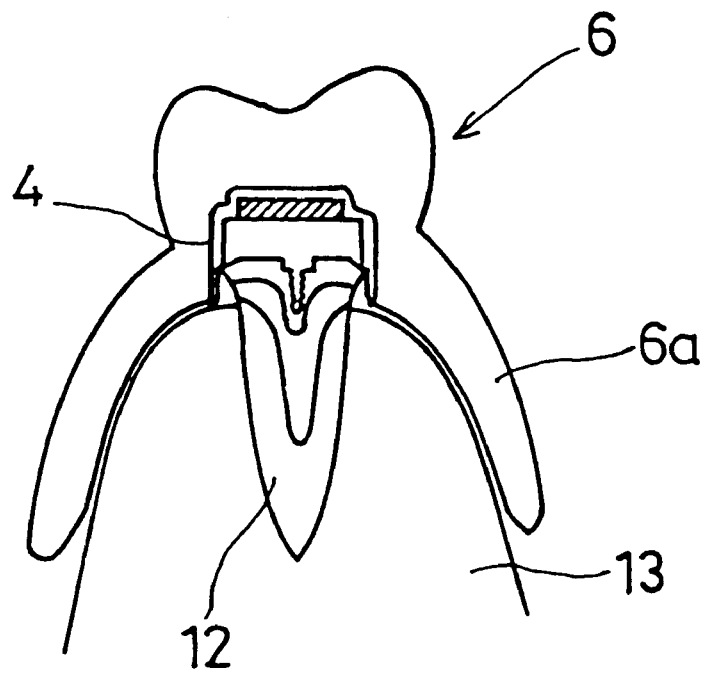
FIG. 13A is a diagram for explaining a difference between the case in which the cap-type magnetic assembly is used for a denture and the case in which the cap-type magnetic assembly is not used for a denture.
Figure 13B:
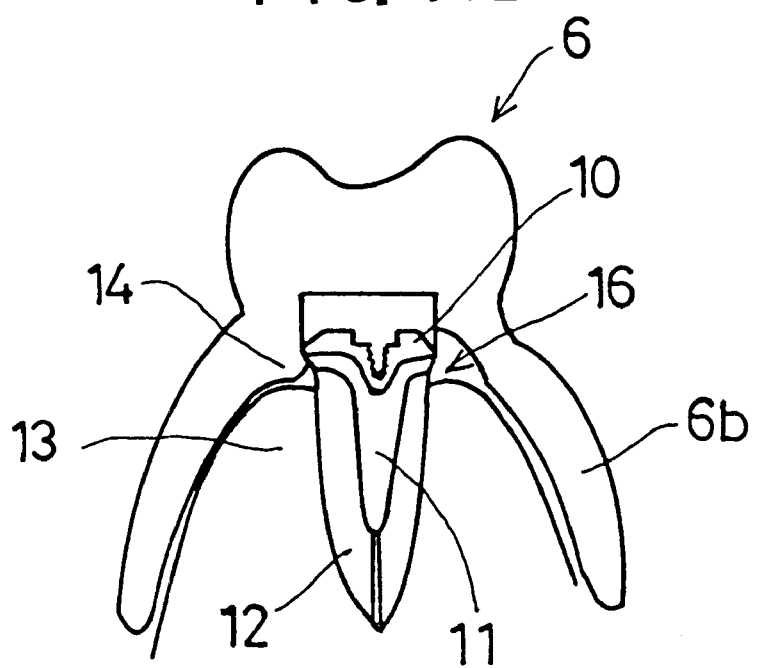
FIG. 13B is a diagram for explaining a difference between the case in which the cap-type magnetic assembly is used for a denture and the case in which the cap-type magnetic assembly is not used for a denture.

FIGS. 13A and 13B are diagrams for explaining a difference between the case in which the cap-type magnetic assembly is used for a denture (FIG. 13A) and the case in which the cap-type magnetic assembly is not used for a denture (FIG. 13B).

As shown in FIG. 13A, when a denture portion 6 is attached via the cap-type magnetic assembly, the resin base 6a of the denture portion 6 and the cap portion 4 of the cap-type magnetic assembly 2 may be adhered without any problems. When the denture portion 6 is attached without having the cap-type magnetic assembly as shown in FIG. 13B, on the other hand, problems such as a generation of an unwanted void 16 between the tooth root 12 and the intermediate metal part 10 or between the root cap 11 and the gingival tissues 13 may occur in addition to the above-mentioned problem in which the self-hardening resin flows into a portion 14.

Therefore, by using the cap-type magnetic assembly according to the present invention as shown in FIG. 13A, the above-mentioned problems may be eliminated.

FIGS. 14A through 14E are diagrams for showing a variation of the male part of the attachment (the keeper) according to the present invention. FIG. 14A shows a keeper 20 having a larger height "h", and FIG. 14B shows a keeper 21 having a smaller height "h". The keeper 20 may be used for a so-called positive retainer and the keeper 21 may be used for a so-called non-positive retainer. The term "positive retainer" means that the binding force between a dental prosthesis and an abutment may be enhanced by the use of the retainer and a load applied to the abutment may also be increased. The term "non-positive retainer" means that the binding force between a dental prosthesis and an abutment may be kept moderate by the use of the retainer and not much load is applied to the abutment.

FIG. 14C shows a keeper 22 which has an inclined (tapered) side surface, FIG. 14D shows a keeper 23 which has a curved side surface, and FIG. 14E shows a keeper 24 which has a curved head portion. The shape of the male part of the attachment may be selected in accordance with a condition of the abutment or a certain clinical objective so that any load applied to the male part of the attachment may be attenuated. In addition, FIG. 14F shows a magnet 25 which may be incorporated in a female part of the attachment and used in combination with the male part of the attachment (keeper) shown in FIG. 14E. Since the magnet 25 has a shape which matches the shape of the head portion of the keeper 24, it is considered that the magnet 25 and the keeper 24 are more strongly attracted due to the increased contacting surface.

Next, a variation of the female part of the attachment (cap-type magnetic assembly) according to the present invention will be described with reference to FIGS. 15A through 15E. In the figures, the cap is shown in combination with a respective keeper.

FIG. 15A shows a cap-type magnetic assembly 30 by which a keeper is firmly covered. This type of cap-type magnetic assembly is suitable for use in the positive retainers. FIGS. 15B and 15C show a cap-type magnetic assembly 31 having an inclined (tapered) side surface and a cap-type magnetic assembly 32 having a curved side surface, respectively. They are suitable in use for the non-positive retainers.

FIG. 15D shows a cap-type magnetic assembly 33 by which a space is intentionally formed between a cover portion 33a of the cap-type magnetic assembly 33 and the side surface of the keeper. In this manner, a force acting on the cap-type magnetic assembly 33 may be released in the side direction. FIG. 15E shows a cap-type magnetic assembly 34 having a spacer 34b inside thereof as shown in the figure. The cap-type magnetic assembly 34 is adhered to a dental prosthesis such as a denture while the spacer 34b is present between the cap 34 and the keeper, and after that the spacer is removed. In this way, a force applied to the cap-type magnetic assembly 34 and the keeper in a vertical direction during the use of the dental prosthesis may be attenuated. In addition, FIG. 15F is a diagram showing a cap-type magnetic assembly 35 which may be used in combination with the keeper 24 shown in FIG. 13E. The cap-type magnetic assemblies other than 35, i.e., 30, 31, 32 and 34 may be applied to any one of the keepers 20, 21, 22 and 23 according to a condition of the abutment or a certain clinical objective.

Figure 16A:
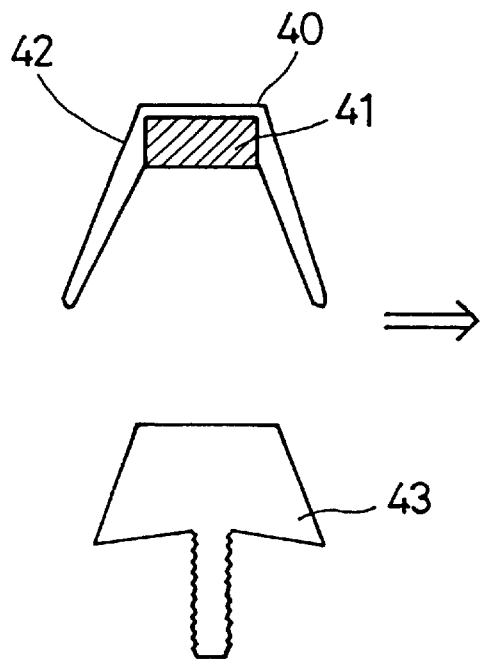
FIG. 16A is a diagram for explaining a modified embodiment of a cap-type magnetic assembly of the magnetic attachment according to the present invention.
Figure 16B:
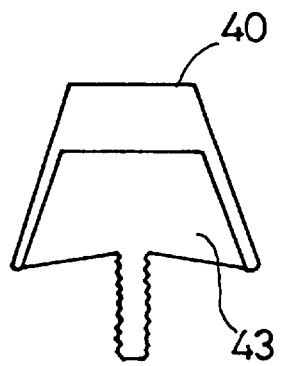
FIG. 16B is a diagram for explaining a modified embodiment of a cap-type magnetic assembly of the magnetic attachment according to the present invention.

FIGS. 16A and 16B are diagrams for explaining a modified embodiment of a cap-type magnetic assembly 40 of the magnetic attachment according to the present invention. In this embodiment, the cap-type magnetic assembly 40 shown in FIG. 16A is comprised of a magnet 41 and a cap portion 42 made of a metal. The cap-type magnetic assembly 40 is characterized by a long inclined cover portion whose shape matches to the shape of a head of a keeper 43 shown in the same figure. The attachment state of the cap-type magnetic assembly 40 and the keeper 43 is shown in FIG. 16B. This type of attachment is suitable for a use in positive retainers.

Any materials appropriate for use in forming a cap portion of the cap-type magnetic assembly (i.e., female part of attachment) may be employed according to the present invention. Examples of such materials include resins such as epoxy type resin; metals such as dental casting ferromagnetic alloys; and elastic materials such as rubber.

As mentioned above, there are three possible combinations of the female part of attachment and the male part of attachment, (namely, magnetic metal magnet; magnet-magnetic metal; and magnet-magnet), and all of the combinations may be applied for use in dental prostheses such as a denture, a crown, a crown-and-bridge set, etc., and in a method for taking an impression.

Figure 17A:
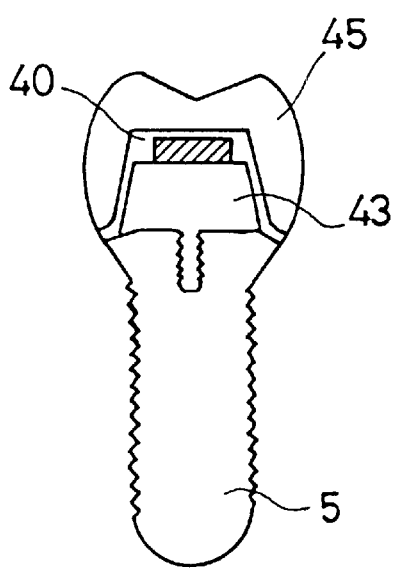
FIG. 17A is a diagram for showing an embodiment in which the magnetic attachment shown in FIG. 16B is used to fix a crown.
Figure 17B:
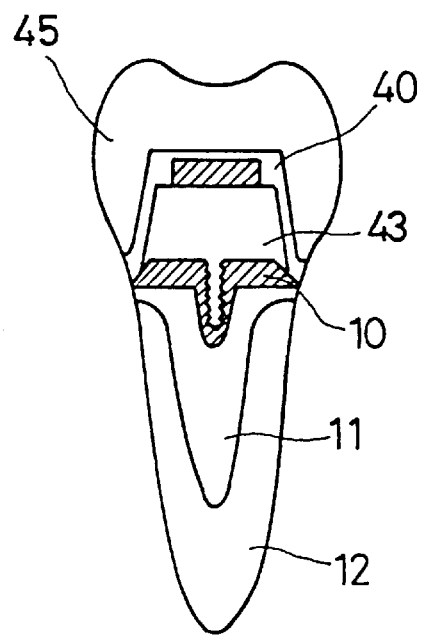
FIG. 17B is a diagram for showing an embodiment in which the magnetic attachment shown in FIG. 16B is used to fix a crown.

FIGS. 17A and 17B are diagrams showing embodiments in which the magnetic attachment shown in FIG. 16B is used to fix a crown 45. In FIGS. 17A and 17B, elements which are the same as the ones in previous figures are indicated by the same reference numerals and the explanation thereof will be omitted. FIG. 17A shows a case in which the magnetic attachment is applied to an implant 5 and FIG. 17B shows a case in which the magnetic attachment is applied to a natural tooth.

The crown 45 may be cemented to the cap-type magnetic assembly 40 using a proper cementing material so as to make the crown 45 removable. Likewise, a removable crown-and-bridge set may be easily constructed using the cap-type magnetic assembly 45. For the construction of the crown-and-bridge set, the female part of attachment may not necessarily be used.

FIG. 18 is a diagram showing another modified embodiment of the magnetic attachment according to the present invention. Although it has been described that a keeper forms a male part of an attachment and a cap-type magnetic assembly (or a cap-type magnetic metal assembly) forms a female part of the attachment in this specification, the relationship is reversed in this embodiment and a cap-type keeper forms a female part of an attachment and a supporting member having a magnet forms a male part of the attachment. Thus, as shown in FIG. 18, a magnet 52 is located in the supporting member 51 which is comprised of a head portion 51a and a screw portion 51b. The supporting member 51 is driven into, for instance, a screw hole of an implant or an intermediate metal. On the other hand, a keeper 50 has a cap shape and forms a female part of attachment. The portion of the keeper 50 which contacts the magnet 52 may be made by a magnet or a magnetic stainless steel. Other portions of the keeper 50 may be made of the same material or a non-magnetic material. This type of magnetic attachment may be suitable for use in a removable crown or a removable crown-and-bridge set.

Moreover, the magnetic attachment shown in FIG. 18 may be applied to a clinical case, in which there is no clearance, by using a larger-size magnet having a stronger magnetic force.

Further, since it is possible to directly adhere the female part of the attachment (the keeper in this embodiment) to a crown or a crown-and-bridge set using heat due to an absent of a magnet in the female part of the attachment, the precision in positioning the crown or crown-and-bridge set may be improved. In particular, since a marginal portion may be made in advance using the female part when an implant is used, a removable crown or a bridge having high precision may be fabricated. Also, the same operation may be performed on a natural tooth using an intermediate metal.

FIGS. 19A through 19C are diagrams showing embodiments in which the magnetic attachment shown in FIG. 18 is applied to fix the crown 46. In these figures, elements which are the same as the ones in previous figures are indicated by the same reference numerals and the explanation thereof will be omitted.

FIG. 19A shows a case in which the magnetic attachment is applied to an implant, FIG. 19B shows a case in which the magnetic attachment is fixed to a root cap 11 via a supporting member 51 having an intermediate metal 10 and FIG. 19C shows the same case as in FIG. 19B except that the diameter of the intermediate metal 10 is smaller than the width of a tooth root 12.

The female part of the attachment according to this embodiment may be heat-adhered to the crown 46. Since a magnet cannot tolerate a strong heat and a conventional magnetic attachment has a magnet in a female part of the attachment, it was not possible to heat-adhere the female part to a crown using a conventional magnetic attachment. According to this embodiment of the present invention, however, that process may be performed since a magnet is put in the male part of the attachment, not in the female part of the attachment.

Figure 20A:
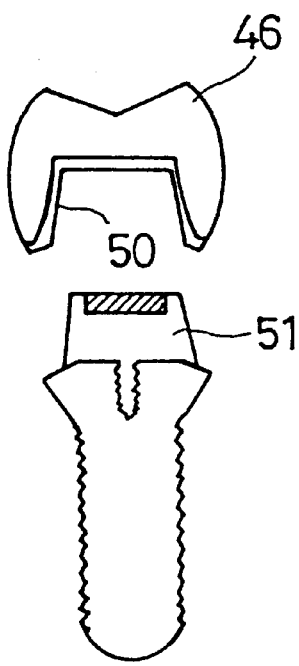
FIG. 20A is a diagram for showing the magnetic attachment and the crown shown in FIG. 19A in a detached state.
Figure 20C:
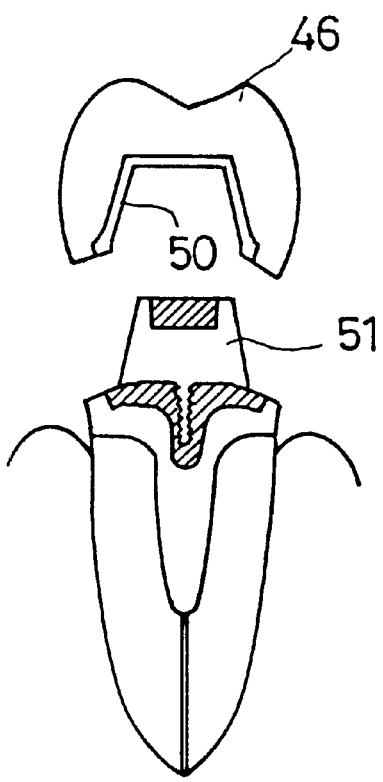
FIG. 20C is a diagram for showing the magnetic attachment and the crown shown in FIG. 19C in a detached state.
Figure 20B:
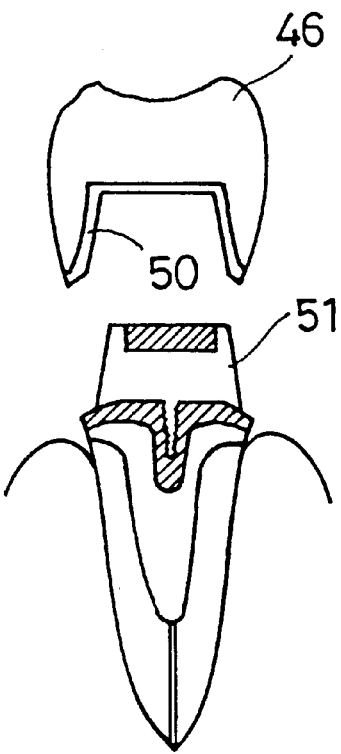
FIG. 20B is a diagram for showing the magnetic attachment and the crown shown in FIG. 19B in a detached state.

FIGS. 20A through 20C are diagrams showing the magnetic attachment and the crown 46 shown in FIGS. 19A through 19C, respectively, in a detached state. As shown in these figures, the crown 46 may be easily removed from the supporting member 51 without rotating the crown 46 nor the supporting member 51.

Figure 21:
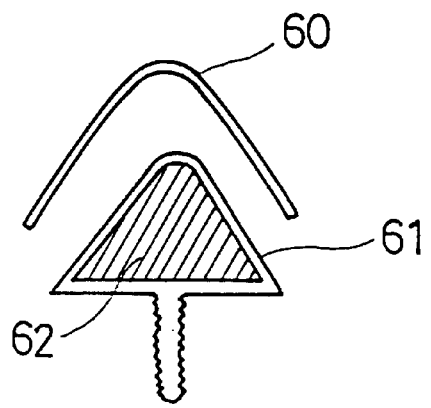
FIG. 21 is a diagram showing another embodiment according to the present invention in which a dental keeper forms a female part of a magnetic attachment and a supporting member including a magnet forms a male part of the magnetic attachment.

FIG. 21 is a diagram showing another embodiment according to the present invention in which a dental keeper 60 forms a female part of an attachment and a supporting member 61 having a magnet 62 forms a male part of the attachment. In this embodiment, the supporting member 61 is formed in a half-spherical or conical shape and the magnet 62 having substantially the same shape in a smaller size as the supporting member is located inside of the supporting member 62. The shape of the keeper 60 is determined to fit the shape of a head portion of the magnet supporting member 61. The magnetic attachment of this type is suitable for non-positive retainers and has an increased surface area for an attachment, with a decreased directionality. Thus, the magnetic attachment may be used together with a retainer which has a strong directionality or in a case that the standing direction of the abutment is not proper for a particular operation. Moreover, the magnetic attachment of this embodiment may be applied to a crown, a bridge, an overdenture, etc.

FIGS. 22A through 22H are diagrams for explaining a method for taking an impression using the magnetic attachment according to the present invention.

Figure 22A:
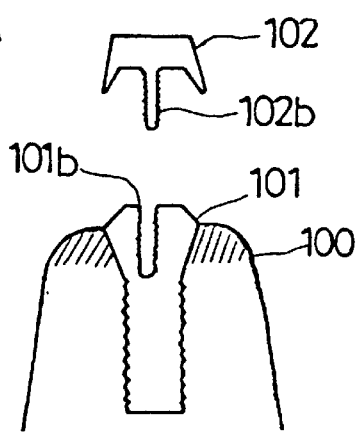
FIG. 22A is a diagram for explaining a method for taking an impression using the magnetic attachment according to the present invention.

First of all, a keeper 102 (male part of attachment) is driven into a screw hole 101b of an abutment (in this case an implant 101) using a screw portion 102b of the keeper 102 or, if the keeper has no screw portion, a screw member, in the oral cavity as shown in FIG. 22A. The numeral 100 indicates a gum. Then, a cap-type magnetic assembly 103 having a magnet portion 103a is attached to the keeper 102 using a magnetic force as indicated by FIG. 22B. The outer surface of the assembly 103 may be undercut so that it would be firmly fixed to an impression material such as an agar impression material and a plaster impression material.

After that, an impression tray 105 on which the impression material 106 has been applied is pressed to the cap-type magnetic assembly 103 and the condition is maintained until the impression material is cured. This is shown in FIG. 22C.

Figure 22E:
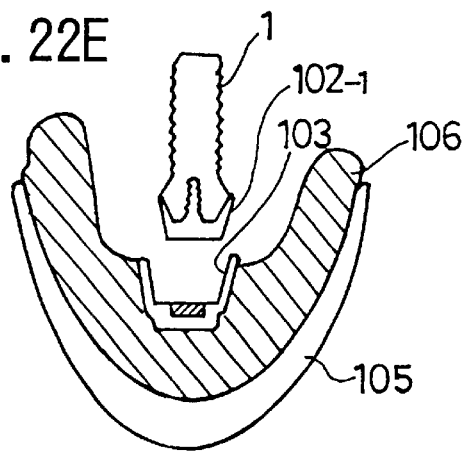
FIG. 22E is a diagram for explaining a method for taking an impression using the magnetic attachment according to the present invention.
Figure 22B:
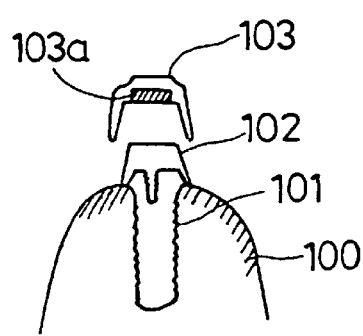
FIG. 22B is a diagram for explaining a method for taking an impression using the magnetic attachment according to the present invention.
Figure 22F:
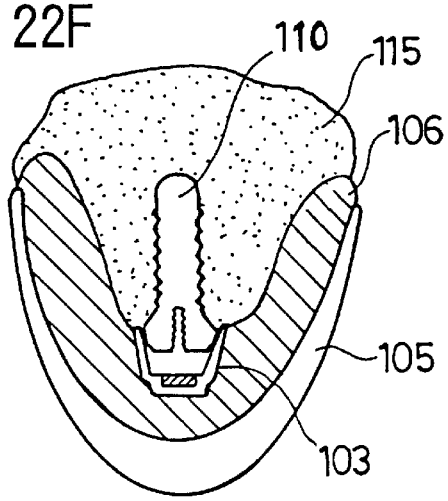
FIG. 22F is a diagram for explaining a method for taking an impression using the magnetic attachment according to the present invention.
Figure 22C:
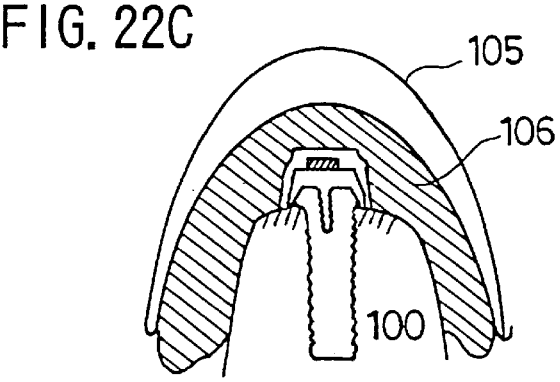
FIG. 22C is a diagram for explaining a method for taking an impression using the magnetic attachment according to the present invention.
Figure 22G:
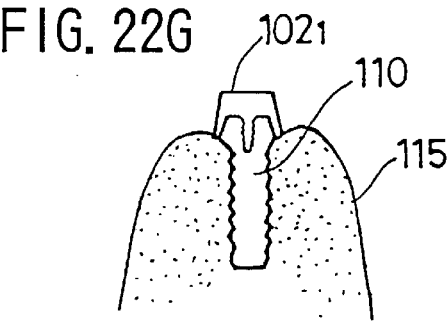
FIG. 22G is a diagram for explaining a method for taking an impression using the magnetic attachment according to the present invention.
Figure 22D:
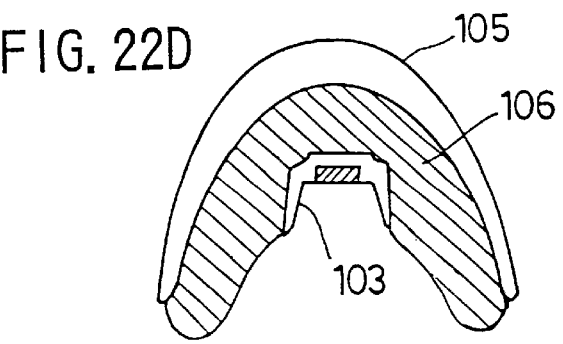
FIG. 22D is a diagram for explaining a method for taking an impression using the magnetic attachment according to the present invention.

When the impression tray 105 is taken out from the oral cavity after the impression material 106 is cured, the cap-type magnetic assembly 103 is detached from the keeper 102 and remains in the impression material 106 as shown in FIG. 22D.

Then, an analog 110 of the implant 101, to which the same type of keeper $102_1$ shown in FIG. 22A is fixed, is attached to the cap-type magnetic assembly 103 in the impression material 106 as indicated by FIG. 22E using the magnetic force and the analog 110 is covered by plaster 115 as shown in FIG. 22F.

Figure 22H:
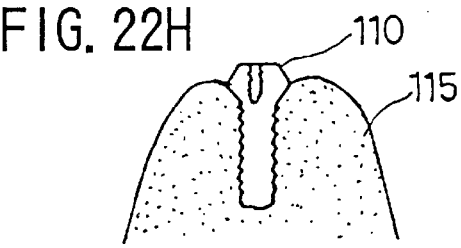
FIG. 22H is a diagram for explaining a method for taking an impression using the magnetic attachment according to the present invention.

After the plaster 115 is dried, it is taken out from the impression material 106 as shown in FIG. 22G and the keeper 102₁ is removed from the analog 110 of the implant 101 to form a replica which may be precisely reproduce the aspect of the implant 101 in the oral cavity as shown in FIG. 22H. By using this replica, a dental prosthesis may be fabricated outside the oral cavity with high precision.

Although the above embodiment is explained using a keeper which forms a male part of an attachment and a cap-type magnetic assembly which forms a female part of the attachment, it is understood that the above embodiment may be performed using a cap-type keeper which forms a female part of an attachment and a supporting member which forms a male part of the attachment as shown in FIGS. 18 and 21.

As explained above, according to the method for taking an impression of the present invention, the process is simplified compared with a conventional method for taking an impression and the aspect of the abutment in the oral cavity can be precisely reproduced.

Now, other embodiments of a member comprising a magnetic attachment according to the present invention will be described.

Figure 23:
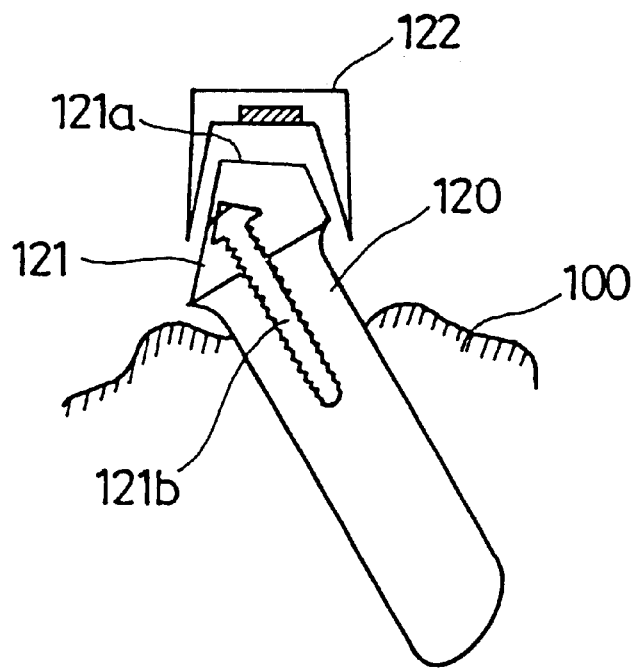
FIG. 23 is a diagram showing a magnetic attachment according to the present invention, which may be applied to an implant fixed to a root of a tooth in an inclined state.

FIG. 23 is a diagram showing a magnetic attachment according to the present invention, which may be applied to an implant fixed to a root of a tooth in an inclined state. Note that the magnetic attachment may also be applied to natural teeth.

In order to perform a firm attachment of a dental prosthesis with an abutment, it is desirable that the upper surface 121a of a male part of a magnetic attachment 121 be reasonably horizontal even when an implant 120 is fixed in an inclined state as shown in the figure. Thus, the male part of the magnetic attachment 121, which is fixed to the implant by a removable fixing member 121b, has a shape by which a predetermined angle is formed by the upper surface 121a and the long axis of the implant 120. A female part of the magnetic attachment 122 may be attached to the male part 121 has an ordinary cap shape and its cap portion firmly covers the male part 121 (in some cases the female part 121 may not necessary be used).

Thus, according to the present invention, the attachment of a male part and a female part is secured, even if an implant is fixed in an inclined state, by using a male portion having a shape appropriate for an occasion.

Figure 24:
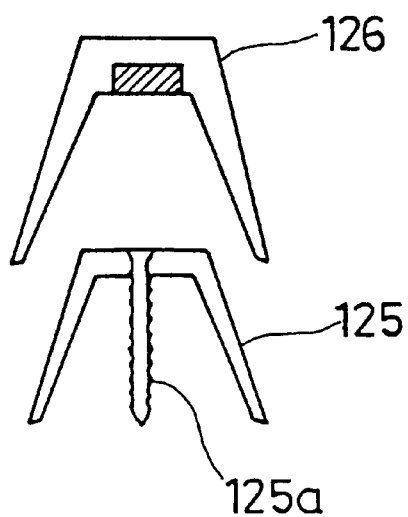
FIG. 24 is a diagram showing an another embodiment of the male part of the magnetic attachment according to the present invention.

FIG. 24 is a diagram showing another embodiment of the male part of a magnetic attachment according to the present invention. As shown in FIG. 24, a male part 125, which may be fixed by a fixing member 125a, has a cap shape that may be engaged with a female part 126. The cap-shape male part 125 of the magnetic attachment according to this embodiment is particularly useful for a case in which the head portion of an implant is projected or a case in which a member projecting from an implant is permanently fixed.

Figure 25A:
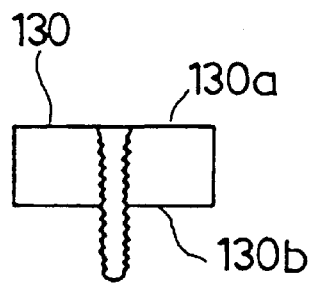
FIG. 25A is a diagram showing a typical example of a member which is used for retaining a dental prosthesis.
Figure 25B:
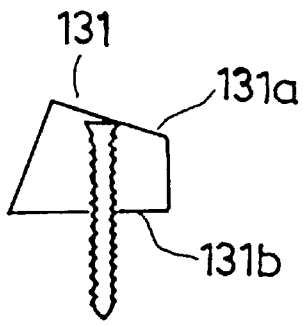
FIG. 25B is a diagram showing another typical example of a member which is used for retaining a dental prosthesis.
Figure 25C:
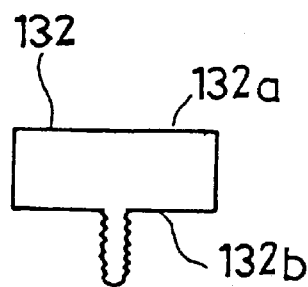
FIG. 25C is a diagram showing another typical example of a member which is used for retaining a dental prosthesis.

FIGS. 25A through 25C are diagrams showing typical examples of a member which is fixed to an abutment and is used for retaining a dental prosthesis by a magnetic force. A male part 130 shown in FIG. 25A has a standard shape in which an upper surface 130a and a lower surface 130b are formed parallel to each other. A male part 131 shown in FIG. 25B, on the other hand, has an irregular shape which is suitable for a case in which an implant is fixed in an inclined state as shown in FIG. 23. A male part 132 shown in FIG. 25B is a self-rotation type male part which does not include a detachable fixing member shown in FIGS. 25A and 25B. In addition, a groove or undercut portion may be formed on the surface of the all of the member described above in order to prevent the rotation of the member.

FIGS. 26A through 26G are diagrams for showing a variation of the member which is fixed to an abutment and used for retaining dental prosthesis by a magnetic force (male part of attachment). In FIGS. 26A through 26E, shaded portions indicate a magnet or a magnetic member.

Figure 26A:
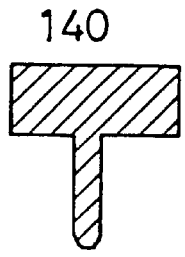
FIG. 26A is a diagram for showing a variation of the male part of the magnetic attachment according to the present invention.
Figure 26B:
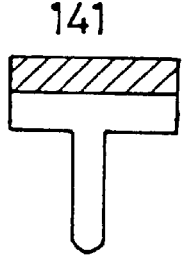
FIG. 26B is a diagram for showing a variation of the male part of the magnetic attachment according to the present invention.
Figure 26C:
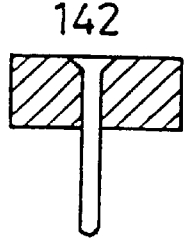
FIG. 26C is a diagram for showing a variation of the male part of the magnetic attachment according to the present invention.
Figure 26D:
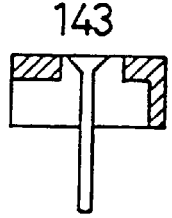
FIG. 26D is a diagram for showing a variation of the male part of the magnetic attachment according to the present invention.

The whole structure of a male part 140 shown in FIG. 26A is comprised of a magnetic member. The upper portion of a male part 141 shown in FIG. 26B is comprised of a magnet or a magnetic member and the lower portion including a fixing portion of the male part 141 is comprised of a non-magnetic metal. The whole structure of a male part 142 shown in FIG. 26C is comprised of a magnet or a magnetic member and it is fixed by a removable fixing member which is made of a non-magnetic member (or magnetic member depending on the condition). The upper portion and/or a part of a side portion of a male part 143 shown in FIG. 26D is comprised of a magnet or a magnetic member and it is fixed by a removable fixing member which is made of a non-magnetic member. The upper portion of a male part 144 shown in FIG. 26E and the upper portion of its fixing member is comprised of a magnet or a magnetic member.

Figure 26E:
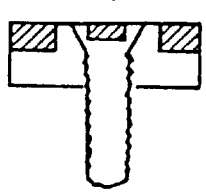
FIG. 26E is a diagram for showing a variation of the male part of the magnetic attachment according to the present invention.

As shown in the above FIGS. 26B, 26D and 26E, when the male part is partially made of a magnet or a magnetic member and the fixing member is comprised of a non-magnetic member, it is possible to improve an anti-corrosive property of the male part.

Figure 26F:
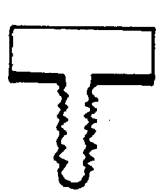
FIG. 26F is a diagram for showing a variation of the male part of the magnetic attachment according to the present invention.
Figure 26G:
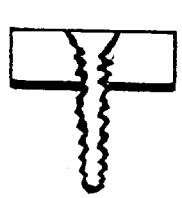
FIG. 26G is a diagram for showing a variation of the male part of the magnetic attachment according to the present invention.

The lower surface including the surface of a fixing member of a male part 145 shown in FIG. 26F is covered by a metal coating which has an anti-corrosive property. Likewise, the lower surface of a male part 146 shown in FIG. 26G and the surface of its fixing member, except its upper surface, is covered by a metal coating having an anti-corrosive property. According to the above embodiments, the strength of the male part may be improved and it can be protected from corrosion, which may be generated from a gap between the male part and a member into which the male part is driven, during a long-term use.

As explained above, according to the present invention, a magnetic attachment comprising a male part, which is fixed to an abutment, and a female part, which is used for a dental prosthesis, and a method for taking an impression using a magnetic attachment is provided. The male part of the magnetic attachment is used as a keeper for retaining a magnetic assembly except some cases (as shown in FIGS. 18 through 21) and the female part is a cap-type magnetic assembly including a cap portion and a magnet. However, the magnetic attachment according to the present invention is not limited as above, and it is possible to provide a magnet with the male part and make the female part a keeper comprised of a magnetic member. Also, as mentioned above, resins, metals or elastic members may be used for forming the cap portion.

In addition, although the cases in which the male part of the magnetic attachment is used in combination with the female part have been described, it is possible to use the male part as a magnetic member, which may be used singly and not in combination with a female part, or as a member for retaining a keeper with a magnetic force.

Also, it is obvious that the present invention is not limited to the above-mentioned embodiments, and variations and modifications may be made without departing from the scope of the present invention.

What is claimed is:

1. An intermediate metal member for removably fixing one of a magnet and a magnetic member to a natural tooth, wherein said intermediate metal member is formed as a unitary, single piece component having a lower fixing portion, said fixing portion projecting from said intermediate metal member to extend into the tooth and being formed to engage the tooth and removably fix the intermediate metal member to the tooth, said intermediate metal member having an upper surface, and wherein said upper surface comprises one of a male and female engagement member to mechanically engage one of the magnet and magnetic member to prevent displacement of said one of the magnet and magnetic member along a direction of extension of said male or female engagement member and secure said one of magnet and magnetic member to said intermediate metal member while allowing said one of said magnet and magnetic member to be easily removed from said intermediate metal member when desired.

2. The intermediate metal member as claimed in claim 1, wherein said intermediate metal member is used in combination with one of said magnet and magnetic member and another one of a magnet and magnetic member, said another one of a magnet and magnetic member covering one of said magnet or magnetic member.

3. An intermediate metal member as claimed in claim 2 wherein said intermediate metal member is used in combination with one of said magnet and magnetic member that comprises a head portion and an attachment member which is used to removably secure said head portion on said intermediate metal member, and wherein said head portion has a sufficient length to project above the tooth when said intermediate metal member is fixed to the tooth.

4. The intermediate metal member as claimed in claim 1, wherein said upper surface comprises a female engagement member.

5. The intermediate metal member as claimed in claim 1, wherein said upper surface comprises a male engagement member.

6. The intermediate metal member as claimed in claim 1, further comprising undercut portions formed in the lower fixing portion, said undercut portions contacting the natural tooth.

7. A magnetic member used in dentistry and suitable for attachment to another magnetic member fixed to an existing structure in a mouth of a subject, said magnetic member comprising:
  a base portion and a cover portion depending from the base portion around the periphery of the base portion to form a cap-like female member containing a magnet, said base portion and cover portion covering said another magnetic member when the magnetic member and said another magnetic member are attached, said base portion incorporating said magnet to form an interior surface that is essentially flat in its entirety, said cover portion having a sufficient length to extend into contiguity with the existing structure when the magnetic member and said another magnetic member are attached, said base and cover portions being formed of one of a resin, a metal, and an elastic member.

8. The magnetic member as claimed in claim 7, wherein said cover portion is formed to contact a sidewall of said another magnetic member when attached to said another magnetic member.

9. The magnetic member as claimed in claim 7, wherein said cover portion is formed to be spaced apart from a sidewall of said another magnetic member when attached to said another magnetic member.

10. The magnetic member as claimed in claim 7, wherein said cover portion is straight along its length.

11. The magnetic member as claimed in claim 7, wherein said cover portion diverges along its length.

12. The magnetic member as claimed in claim 7, further comprising a spacer attached to the cover portion.

13. The magnetic member as claimed in claim 7, wherein the base portion comprises a magnet.

14. The magnetic member as claimed in claim 13, wherein the base portion comprises a magnet that has a surface that is exposed to contact said another magnetic member.

15. An intermediate metal member for removably fixing one of a magnet and a magnetic member to a natural tooth, wherein said intermediate metal member is formed as a unitary, single piece component having a lower fixing portion, said fixing portion projecting from said intermediate metal member to extend into the tooth and being formed to engage the tooth and removably fix the intermediate metal member to the tooth, said intermediate metal member having an upper surface, wherein said upper surface comprises one of a male and female engagement member to mechanically engage one of the magnet and magnetic member and removably secure said one of magnet and magnetic member to said intermediate metal member, and wherein said upper surface has a step portion for receiving a corresponding step portion of one of a magnet and magnetic member.

16. The intermediate metal member as claimed in claim 15, wherein said upper surface comprises a female engagement member.

17. The intermediate metal member as claimed in claim 15, wherein said upper surface comprises a male engagement member.

18. An intermediate metal member for removably fixing one of a magnet and a magnetic member to a natural tooth, wherein said intermediate metal member is formed as a unitary, single piece component having a lower fixing portion, said fixing portion projecting from said intermediate metal member to extend into the tooth and being formed to engage the tooth and removably fix the intermediate metal member to the tooth, said intermediate metal member having an upper surface, and wherein said upper surface has a screw hole formed therein to receive a thread portion of the magnet and magnetic member and removably secure said one of magnet and magnetic member to said intermediate metal member.

19. The intermediate metal member as claimed in claim 15 or 18, wherein said intermediate metal member is used in combination with one of said magnet and magnetic member and another one of a magnet and magnetic member, said another one of a magnet and magnetic member covering one of said magnet or magnetic member.

20. An intermediate metal member as claimed in claim 19 wherein said intermediate metal member is used in combination with one of said magnet and magnetic member that comprises a head portion and an attachment member which is used to removably secure said head portion on said intermediate metal member, and wherein said head portion has a sufficient length to project above the tooth when said intermediate metal member is fixed to the tooth.

21. The intermediate metal member as claimed in claim 15 or 18, further comprising undercut portions formed in the lower fixing portion, said undercut portions contacting the natural tooth.

22. An impression-taking member used for taking an impression in dentistry and employing a magnetic force, said member comprising:
  a male part having a fixing member adapted to fix the male part in an existing structure in a mouth of a subject, said male part having a projecting head portion; and a female part receiving said head portion of said male part, said female part having a cover portion for covering said head portion and extending into contiguity with the existing structure around said male part when said male part is received in said female part, one of said male part and female part having a magnet, the other of said male and female part having means magnetically attracted to said magnet for removably retaining said male part and female part together, said female part having a base portion having a periphery from which said cover portion depends, said base portion incorporating said one of said magnet or magnetically attracted means and presenting an internal surface in said female part which is essentially flat in its entirety, the cover portion of said female part being adapted to receive impression material applied to the existing structure when the male part and female part are retained together by the magnetic force, the contiguity of the cover part with the existing structure in the mouth of the subject ensuring that the impression material can be drawn off the existing structure without interference.

23. The impression-taking member as claimed in claim 22 wherein the male part is further defined as adapted to be fixed to an existing structure comprising one of a natural tooth, an implant for a tooth, and a member connected to an implant for a tooth.

24. The impression-taking member as claimed in claim 22, wherein said fixing member is detachable from said projecting head portion.

* * * * *